United States Patent [19]

Glunz et al.

[11] E Re. 30,376

[45] Reissued * Aug. 19, 1980

[54] 8-METHOXYPSORALEN

[75] Inventors: Louis J. Glunz; Donald E. Dickson, both of Chicago, Ill.

[73] Assignee: Thomas C. Elder, Inc., Hamilton, Ind.

[ * ] Notice: The portion of the term of this patent subsequent to Dec. 12, 1995, has been disclaimed.

[21] Appl. No.: 68,011

[22] Filed: Aug. 20, 1979

Related U.S. Patent Documents

Reissue of:

[64] Patent No.: 4,129,575
Issued: Dec. 12, 1978
Appl. No.: 676,302
Filed: Apr. 12, 1976

[51] Int. Cl.[2] ..... C07D 311/78
[52] U.S. Cl. ..... 260/343.21; 260/346.22
[58] Field of Search ..... 260/343.21

[56] References Cited

PUBLICATIONS

House, Modern Synthetic Reactions, 2nd edition, 1972, pp. 3, 37–40.
Davies et al., Jour. Chem. Soc. 1950, 3202–3206.
Lagercrantz, Acta Chemica Scandinavica, vol. 10, 1956, pp. 647–654.
Fieser and Fieser, Reagents for Organic Syn., p. 293.
Houben-Weyl, Teil 4, p. 284.
Seshadri et al., Indian Jour. Chem., vol. 1(7) 1963, pp. 291–294.

*Primary Examiner*—Henry R. Jiles
*Assistant Examiner*—Jane T. Fan
*Attorney, Agent, or Firm*—Gordon W. Hueschen

[57] ABSTRACT

8-Methoxypsoralen is prepared in six steps from pyrogallol including hydrogenation of [6,7-dihydroxy-2,3-dihydrobenzofuran] *6,7-dihydroxycoumaranone* and dehydrogenation of [2,3] *4',5'*-dihydroxanthotoxin. Improvements in these two steps lead to a marked overall increase in yield.

15 Claims, No Drawings

8-METHOXYPSORALEN

Matter enclosed in heavy brackets [ ] appears in the original patent but forms no part of this reissue specification; matter printed in italics indicates the additions made by reissue.

BACKGROUND OF INVENTION

PRIOR ART

This invention relates to the manufacture of 8-methoxypsoralen and is directed to improvements in a process in which pyrogallol is converted to 8-methoxypsoralen in six unit process steps.

Lagercrantz, Acta Chemica Scandinavica Vol. 10, (1956) pp. 647–654 reports the preparation of 8-methoxypsoralen in the following six unit process steps beginning with pyrogallol:

(1) Pyrogallol is reacted with chloracetic acid in the presence of phosphorus oxychloride to form ω-chloro-2,3,4-trihydroxyacetophenone, (2) which product is cyclized by the splitting off [hydrochloric acid] *of hydrogen chloride* to form 6,7-dihydroxycoumaranone, (3) which product is hydrogenated with hydrogen over a palladium catalyst in acetic acid at 1 atmosphere and 65° C. [,] *to form 6,7-dihydroxy-2,3-dihydrobenzofuran,*

(4) which product is reacted with malic acid in the presence of concentrated sulphuric acid to form [2,3-dihydroxanthotoxol] *4',5'-dihydroxanthotoxol,*

(5) which product is methylated using diazomethane to form [2,3-dihydroxanthotoxin] *4',5'-dihydroxanthotoxin,*

(6) which product is dehydrogenated with palladium catalyst in boiling diphenyl ether to form the desired 8-methoxypsoralen (xanthotoxin).

Davies et al., J. Chem. Soc., (1950), 3202–6 reports the first two of these unit process steps and Späth et al., Ber. 69, (1936), 767–770, reports the last four of these steps.

The overall yield in these prior art processes is less than about 3 percent. This is due to the relatively low yield in some or most of the unit process steps. The problem steps apparently are the hydrogenation step (3) and the dehydrogenation step (6). In regard to the former, Späth obtained 33 percent yield and Lagercrantz, 50 percent yield. However, Lagercrantz points out that this unit process is highly critical, that the hydrogenation also involves enolization of the oxo group and that the starting 6,7-dihydroxycoumaran-3-one (hereinafter referred to as 6,7-dihydroxycoumaranone) must be "very pure" in order to avoid poisoning of the catalyst. He suggests recrystallization several times with active carbon. In regard to the dehydrogenation, the best yield reported is 37 percent. This, coupled with the relatively low yields reported for steps 1, 3, and 4, makes the overall yield of the prior art process less than about 3 percent.

OBJECT OF THE INVENTION

It is an object of the invention to provide an improved process for making 8-methoxypsoralen. A further object of the invention is to provide a process which avoids the disadvantages of the prior art. A further object of the invention is to provide an improved process for the hydrogenation of 6,7-dihydroxycoumaranone. A further object of the invention is to provide an improved process for dehydrogenation of [2,3-dihydroxanthotoxin] *4',5'-dihydroxanthotoxin.* A further object of the invention is to provide an improved overall process. Further objects will appear as the description proceeds.

SUMMARY OF THE INVENTION

The invention relates to improvements in a process for making 8-methoxypsoralen from pyrogallol in the following steps:

(1) reacting pyrogallol with chloracetic acid to form ω-chloro-2,3,4-trihydroxyacetophenone, (2) heating ω-chloro-2,3,4-trihydroxyacetophenone in the presence of a hydrogen chloride acceptor to form 6,7-dihydroxycoumaranone, (3) hydrogenating 6,7-dihydroxycoumaranone to form 6,7-dihydroxy-2,3,-dihydrobenzofuran, (4) reacting 6,7-dihydroxy-2,3,-dihydrobenzofuran with malic acid to form [2,3-dihydroxanthotoxol] *4',5'-dihydroxanthotoxol,*

(5–6) methylating and dehydrogenating to convert [2,3-dihydroxanthotoxol] *4',5'-dihydroxanthotoxol* to 8-methoxypsoralen, which improvements comprise a novel procedure for effecting the hydrogenation, a novel procedure for effecting the dehydrogenation, and a general overall combination of particular unit process steps leading to improved overall yield.

In steps 5–6, the methylation can be done first and then the dehydrogenation, or the dehydrogenation first and then the methylation. The latter is of advantage where a tagged or labeled product is desired. Thus, if [2,3-dihydroxanthotoxol] *4',5'-dihydroxanthotoxol* is first converted to xanthotoxol, the xanthotoxol can be methylated with a tagged or labeled methylating agent to form the desired tagged or labeled 8-methoxypsoralen.

Steps 1 and 2 are carried out as described in Lagercrantz and Davies and comparable yields are obtained. Step 3, however, has been modified to give substantially greater yields and to make it possible to avoid the necessity for repeated recrystallization of the starting 6,7-dihydroxycoumaranone. In Step 4, a low reaction temperature and a simplified work-up gives better yields. In Step 5–6, the methylation, the expensive and highly explosive and dangerous diazomethane is replaced by dimethyl sulphate without sacrificing yield and in the dehydrogenation, Step 5–6, use of 2,3-dichloro-5,6-dicyano-1,4-benzoquinone as a dehydrogenation agent results in a two-fold increase in the unit yield of 8-methoxypsoralen. Still higher unit yields are obtained if chlorobenzene is used as the solvent. With these improvements, overall yields greater than 10 percent are obtainable.

The hydrogenation of 6,7-dihydroxycoumaranone in accordance with the invention is effected in a low pressure hydrogenation unit under an absolute pressure of hydrogen of about 2 atmospheres and a temperature of about 100° C. in a mixture of acetic acid and ethyl acetate, advantageously, in the proportions of about five percent to about thirty percent acetic acid. Higher percentages of acetic acid can be used, but only with sacrifice in yields. Also the ethyl acetate can be substituted by other solvents like methanol and ethanol but only with a sacrifice in yields. Higher or lower pressures, say, from about 1 to about 10 atmospheres absolute pressure, and higher or lower temperature, say, from about 65° C. to about 150° C., can be used in accordance with practices already well known for low pressure hydrogenation.

The reaction mixture is cooled and the catalyst is filtered off. The solvent is distilled under reduced pressure leaving an oil which can be used as the starting material in the next step. If desired residual acetic acid can be removed by azeotropic distillation with benzene. Finally, the product is crystallized from an inert solvent, such as benzene, to yield a crude product which can be used directly in the next step. If desired, however, the crude material can be further recrystallized. For this crystallization and recrystallization, any inert solvent for the produced [6,7-dihydroxy-2,3-benzofuran] *6,7-dihydroxy-2,3-dihydrobenzofuran,* can be used but those like benzene, toluene, chlorobenzene, petroleum ether, ethylene chloride, cyclohexane, and the like, in which the product has limited solubility are preferred.

The starting material for Step 3, 6,7-dihydroxycoumaranone, is obtained by refluxing ω-chloro-2,3,4-trihydroxyacetophenone in ethanol in the presence of sodium acetate, distilling off the ethanol and crystallizing the product from water.

The crude product resulting from this crystallization is used directly in the [hydrogen] *hydrogenation* step but, if desired, can be recrystallized from acetone or other suitable inert solvent in which the 6,7-dihydroxycoumaranone has limited solubility.

Alternatively, the cyclization can be effected by heating in the presence of a hydrogen chloride acceptor in a suitable solvent or vehicle. Suitable such hydrogen chloride acceptors include potassium carbonate and exchange resins such as Dow-X 1, Imac A-21, Permutic ES, Amberlite IRA-410, and the like. Ordinarily these ion exchange resins comprise a cross-linked polystyrene base or like cross-linked resin base, substituted by a trimethylbenzylammonium group or like quaternary ammonium groups. Such hydrogen acceptors have the advantage that they are easily separated from the reaction mixture by filtration.

The 6,7-dihydroxy-2,3-dihydrobenzofuran from Step 3 is reacted with malic acid in concentrated sulpuric acid at a temperature of about 80° C. to not more than about 100° C. This temperature, which is substantially lower than that used in the prior art, makes it easier to control foaming and this, coupled with slightly different work-ups, results in higher yields.

The low temperature is determined by that at which the reaction proceeds as evidenced by the evolution of gas, presumably carbon monoxide, and the higher temperature by that at which excessive tar does not form. The action is continued until substantial evolution of gas ceases. Ten minutes or so will ordinarily suffice at temperatures about 100° C., but longer periods may be required at lower temperatures. The desideratum is as low a temperature and as short a time as possible since longer times and higher temperatures result in the formation of more tar and lower yields.

Advantageously, the sulphuric acid is preheated to or near the desired reaction temperature, say to between about 70° C. and about 100° C. To the hot sulphuric acid, a mixture of 6,7-dihydroxy-2,3-dihydrobenzofuran and malic acid is added with stirring while maintaining the temperature between about 80° C. and about 100° C. The proportions are the stoichiometric, advantageously with a slight excess, say up to 10 or 20 percent excess, of malic acid. As the sulfuric acid acts primarily as a dehydrating agent, the amount is not critical as long as sufficient is present for this purpose and to give an easily workable and handleable reaction mixture. The reaction mixture, however obtained, is cooled and poured into ice water and extracted with chloroform. Advantageously, the ice water and the chloroform are premixed so that the product, [2,3-dihydroxanthotoxol] *4',5'-dihydroxanthotoxol,* is extracted into the chloroform before it becomes contaminated with or occluded in any tar that is precipitated.

The chloroform extract is dried with sodium sulphate, concentrated to or near dryness, and washed with a relatively large volume of an inert non-solvent, for example, hexane, filtered and dried. Any inert non-solvent for the product can be used in place of the hexane, for example, any aliphatic or cycloaliphatic hydrocarbon, since it is used here primarily for its physical effect. The resulting crude product is used directly in the following step but, if desired, can be recrystallized from water.

The resulting [2,3-dihydroxanthotoxol] *4',5'-dihydroxanthotoxol* is now methylated with dimethyl sulphate in an inert solvent such as acetone in the presence of an acid acceptor, for example, potassium carbonate. The reaction mixture is drowned in a dilute sodium hydroxide solution and the product recovered by filtration. The crude product thus obtained can be used directly in the next step but, if desired, can be recrystallized from benzene, or like inert-solvent in which [2,3-dihydroxanthotoxin] *4',5'-dihydroxanthotoxin* has limited solubility.

The [2,3-dihydroxanthotoxin] *4',5'-dihydroxanthotoxin* thus obtained is then dehydrogenated. This advantageously is effected by heating the [2,3-dihydroxanthotoxin] *4',5'-dihydroxanthotoxin* with 2,3-dichloro-5,6-dicyano-1,4-benzoquinone in a substantially inert solvent, for example, toluene or chlorobenzene, advantageously at reflux, until substantial dehydrogenation is obtained. The 2,3-dichloro-5,6-dicyanohydroquinone formed and any residual 2,3-dichloro-5,6-dicyano-1,4-benzoquinone are removed and the product taken up in chloroform and recovered therefrom. If substantial amounts of the residual 2,3-dichloro-5,6-dicyano-1,4-benzoquinone are present, it is desirable to convert this to the corresponding hydroquinone with sodium dithionite, dissolve the hydroquinone in aqueous sodium bicarbonate, and extract the sodium bicarbonate solution with chloroform to recover the 8-methoxypsoralen which can be recovered by drying over sodium sulphate and concentrating to dryness. The resulting product can then be recrystallized from benzene or any suitable inert solvent in which 8-methoxypsoralen has limited solubility. If there is little residual 2,3-dichloro-5,6-dicyano-1,4-benzoquinone, the reaction mixture can be cooled and the precipitated hydroquinone filtered off and the reaction mixture, i.e., the filtrate, then extracted with chloroform. If desired, the filter cake can be extracted with benzene or like solvents such as chlorobenzene, toluene, and the like, for example, by refluxing the filter cake in the solvent and then adding the extract to the reaction mixture filtrate prior to the chloroform extraction. The chloroform solution is then washed successively with dilute sodium bisulfite solution, dilute sodiium bicarbonate solution, and water and dried over sodium sulfate. The resulting chloroform solution is then concentrated by distillation until the product precipitates and an inert non-solvent such as hexane or like aliphatic or cycloaliphatic hydrocarbon is added to cause further precipitation of the product and the product is filtered. If desired, the product can be further purified by redissolving it in chloroform, or chloroform containing a minor amount of ethyl acetate, passing the solution over an alumina column concentrating the effluent until crystallization takes place, adding hexane or like solvent further to cause precipitation of the product, and filtering the solution.

If desired, the last two steps, namely, the methylation and the dehydrogenation can be inverted. In other words, the [2,3-dihydroxanthotoxol] *4',5'-dihydroxanthotoxol,* instead of being methylated, is dehydrogenated to form xanthotoxol and the resulting xanthotoxol methylated to form 8-methoxypsoralen. The same reaction conditions and work-ups can be used as given above for the methylation and dehydrogenation.

DETAILED DESCRIPTION OF THE INVENTION

The following examples are given by way of illustration only. Parts and percentages are by weight unless otherwise specified.

EXAMPLE 1

8-Methoxypsoralen

Part A:

ω-Chloro-2,3,4-trihydroxyacetophenone

A flask equipped with a stirrer and protected from atmospheric moisture was charged with 126.1 g of pyrogallol, 101.1 g chloracetic acid and 101.2 g of phosphorus oxychloride.

The contents were stirred and heated at 60° C. until stirring became quite difficult (approximately 4 hours), hydrogen chloride was evolved during the reaction. The reaction mixture was then cautiously hydrolyzed with ice water (750 ml/mole), and the resulting mixture was heated to 70° C. for 30 minutes and then cooled to 0° C. After stirring at 0° C. for 12 hours, the mixture was filtered to collect the product. The cooled product was washed with a small amount of ice water and dried. Dark tan crystals of ω-chloro-2,3,4-trihydroxyacetophenone melting at 166°–8° C. were obtained in a yield of 55 percent (111 g/mole). This crude product was used directly in the next step without further purification.

On successive replications, the yield varied from 45 to 55 percent.

The crude product on recrystallization from water gave light tan crystals melting at 168°–170° C.

Part B:

[6,7-Dihydroxycumaranone]
*6,7-Dihydroxycoumaranone*

A mixture of 1.5 l of ethanol (2B alcohol), 249.1 g sodium acetate and 202.6 g ω-chloro-2,3,4-trihydroxyacetophenone from Part A was refluxed for six hours. The ethanol was distilled off and the residue was treated with 1.5 l of water and was cooled with stirring to −5° to −0° C., filtered, and the product washed with a small amount of ice water and air dried. There was obtained 141 g (85 percent yield), of crude 6,7-dihydroxycoumaranone melting at 230°–2° C. This crude product was used in Step C.

On successive replications, the yield varied from 76 to 85 percent.

On recrystallization from acetone there were obtained light tan crystals melting at 232°–4° C.

Part C:

6,7-Dihydroxy-2,3-dihydrobenzofuran

A low pressure hydrogenation unit was charged with 4 l of a 20 percent acetic acid solution in ethyl acetate, 55 g of 10 percent palladium on carbon and 166.1 g of the crude 6,7-dihydroxycoumaranone of Part B. Hydrogen was admitted under 30 psi [guage] *gauge* pressure and at a temperature of 100° C. until the theoretical amount [(1 mole)] *(2 moles)* of hydrogen was absorbed and further take-up had stopped. This took approximately 12 hours. The reaction mixture was then cooled and filtered to remove the catalyst. The filtrate was distilled under reduced pressure leaving an oil. This oil was taken up in 1 liter of benzene and the benzene distilled off to remove residual acetic acid as a benzene-acetic acid azeotrope. This was repeated two times. Finally the residue was taken up in 500 ml of benzene and the resultant cooled to precipitate out the product. On filtering and washing with a little cold benzene, there was obtained 126 g (83 percent yield), of crude 6,7-dihydroxy-2,3-dihydrobenzofuran melting at 97°–9° C., which was transferred directly as the starting material [as] *of* Step D.

On successive replications, the yield varied from 74 to 83 percent.

On recrystallization from benzene, there were obtained off-white crystals melting at 104°–6° C.

If all the acetic acid is not removed in the azeotropic distillation, an oily residue may remain which is not taken up by the benzene. This oily residue is high in product and can be used successfully in the next step.

Part D:

[2,3-Dihydroxanthotoxol] *4',5'-Dihydroxanthotoxol*

A flask equipped with a stirrer and port thermometer was charged with 460 ml of concentrated sulphuric acid and the temperature was brought to 70° C. A mixture of 152 g of 6,7-dihydroxy-2,3-dihydrobenzofuran from Part C and 154 g of malic acid was cautiously added to the sulphuric acid with stirring while the temperature was brought to 100° C. Carbon monoxide was evolved during the reaction and caused some foaming of the reaction mixture. The reaction mixture was maintained at 100° C. for 10 minutes at which time the bulk of the gas evolution had ceased. The mixture was then cooled to room temperature and poured into a stirred mixture of 6 liters of water and 12 liters of chloroform. Sometimes material separates which generally remains suspended in the aqueous layer. The chloroform layer was separated and the aqueous *layer* re-extracted two more times with chloroform, first with 6 liters and second with 2 liters. To the combined chloroform extract after drying with sodium sulphate and concentrating the combined chloroform extracts to near dryness, was added 1 liter of hexane and the product filtered and dried. There was obtained 1.2 g (55 percent yield), of crude [2,3-dihydroxanthotoxol] *4',5'-dihydroxanthotoxol* melting at 190°–3° C. This crude product was used in Step E.

On successive replications, the yield varied from 45 to 55 percent.

Upon recrystallization from water, there was obtained off-white crystals melting at 191°–3° C.

Part E:

[2,3-Dihydroxanthotoxin] *4',5'-Dihydroxanthotoxin*

A reaction mixture of 204 g of [2,3-dihydroxanthotoxol] *4',5'-dihydroxanthotoxol* of Part D, 136 g of dimethyl sulphate, 828 g of potassium carbonate, and 9 liters of acetone was refluxed with stirring for 16 hours. The reaction mixture was then cooled and filtered and the filter cake washed with acetone. The acetone solution was concentrated to approximately 2 liters and poured into 4 liters of 1 percent sodium hydroxide solution with good stirring. The product was filtered and washed with water until the pH was neutral. It was then washed with a little cold acetone and finally air dried. There was obtained 185 g (85 percent yield), of crude [2,3-dihydroxanthotoxin] *4',5'-dihydroxanthotoxin* melting at 158°–160° C. This crude product was used directly in Step F.

On successive replications, the yield varied from 80 to 85 percent.

On recrystallization from benzene, there was obtained a white solid melting at 159°–160° C.

Part F-1:

8-Methoxypsoralen

A reaction mixture of 218 g of [2,3-dihydroxanthotoxin] *4',5'-dihydroxanthotoxin* of Part E, 281 g of 2,3-dichloro-5,6-dicyano-1,4-benzoquinone, and 3 liters of toluene was stirred and heated at reflux for 20 hours. The mixture was cooled and poured into 10 liters of 10 percent sodium hydroxide solution containing 5 percent sodium dithionite. The solution was then extracted twice with about 2 liters of chloroform. The combined chloroform extracts were washed with water and dried over sodium sulphate and concentrated to dryness. There was obtained 150 g (70 percent yield), of crude 8-methoxypsoralen which on crystallization from benzene was obtained as white crystals melting at 138°–140° C.

On successive replications, the yield varied from 65 to 70 percent. The overall yield was 13%.

Part F-2:

8-Methoxypsoralen

A reaction mixture of 218 g of [2,3-dihydroxxanthotoxin] *4',5'-dihydroxanthotoxin* of Part E, 250 g of 2,3-dichloro-5,6-dicyano-1,4-benzoquinone, and 2 l of chlorobenzene was stirred at reflux for 12 hours. The reaction mixture was cooled and the precipitated hydroquinone filtered off, the filter cake was extracted with 2 l of benzene at reflux, filtered hot and the extract added to the filtrate. Three l of chloroform was then added and the mixture washed, first, with 2 l of 2 percent sodium bisulfite, second, 2 l of 1 percent sodium bicarbonate, and third, 2 l of water, and then dried over sodium sulphate. The dried solution was then concentrated by distillation until the product precipitated, whereupon 500 ml of hexane was added and the product filtered. The product was then dissolved in 4:1 (v/v) chloroform/ethyl acetate and passed over an alumina column (Neutral Alumina, Brockman Activity 1). The effluent was concentrated until crystallization took place. There was then added 500 ml of hexane and the product was recovered by filtration. White crystals of 8-methoxypsoralen melting at 143.5°–145° C. were obtained in 85 percent yield.

On successive replications, yields of 80 to 85 percent were obtained. The overall yield was 15%.

EXAMPLE 2

8-Methoxypsoralen

Part A:

Following the procedure of Part F-2 of Example 1, substituting the [2,3-dihydroxanthotoxin] *4',5'-dihydroxanthotoxin* by the equivalent amount of [2,3-dihydroxanthotoxol] *4',5'-dihydroxanthotoxol* of Part D of Example 1, there is obtained xanthotoxol.

Part B:

Following the procedure of Part E of Example 1, substituting the [2,3-dihydroxanthotoxol] *4',5'-dihydroxanthotoxol* by the equivalent amount of xanthotoxol from Part A above, there is obtained 8-methoxypsoralen.

Part C:

Following the procedure of Part B above, substituting the dimethylsulfate by tagged or labeled dimethylsulfate, there is obtained tagged or labeled 8-methoxypsoralen.

It is to be understood that the invention is not to be limited to the exact details of operation or structure shown as obvious modifications and equivalents will be apparent to one skilled in the art.

I claim:

1. In a process for making 8-methoxypsoralen from pyrogallol in the following steps:

(1) reacting pyrogallol with chloracetic acid to form ω-chloro-2,3,4-trihydroxyacetophenone, (2) heating ω-chloro-2,3,4-trihydroxyacetophenone in the presence of a hydrogen chloride acceptor to form 6,7-dihydroxycoumaranone, (3) hydrogenating 6,7-dihydroxycoumaranone to form 6,7-dihydroxy-2,3-dihydrobenzofuran, (4) reacting 6,7-dihydroxy-2,3-dihydrobenzofuran with malic acid to form [2,3-dihydroxanthotoxol] *4',5'-dihydroxanthotoxol,*

(5–6) methylating and dehydrogenating to form 8-methoxypsoralen, the improvement which comprises effecting step 3 with elemental hydrogen over a palladium catalyst in a solution of acetic acid in ethyl acetate.

2. The process of claim 1, in which the solvent solution is distilled and the residuum of acetic acid removed by azeotropic distillation with benzene.

3. The process of claim 1, in which hydrogenation is effected at a pressure of about 1 to about 10 atmospheres and a temperature of about 65° to about 150° C.

4. The process of claim 3, in which the catalyst is 10 percent palladium on charcoal and the solvent is a mixture of acetic acid and ethyl acetate containing from about 5 to about 30 percent acetic acid.

5. The process of claim 1, in which the dehydrogenation is effected with 2,3-dichloro-5,6-dicyano-1,4-benzoquinone in a substantially inert solvent.

6. The process of claim 5, in which the inert solvent is toluene.

7. The process of claim 5, in which the inert solvent is chlorobenzene.

8. The process of claim 1, in which the [2,3-dihydroxanthotoxol] *4',5'-dihydroxanthotoxol* of step 4 is methylated with dimethyl sulfate to form [2,3-dihydroxanthotoxin] *4',5'-dihydroxanthotoxin.*

9. The method of claim 8, in which the [2,3-dihydroxanthotoxin] *4',5'-dihydroxanthotoxin* is dehydrogenated with 2,3-dichloro-5,6-dicyano-1,4-benzoquinone in a substantially inert solvent.

10. The process of claim 1, in which the cyclization of step 2 is effected by refluxing ω-chloro-2,3,4-trihydroxyacetophenone with sodium acetate in ethanol, distilling off the ethanol and crystallizing the product from water and in which the resulting product without substantial further purification is used as the starting material for the hydrogenation of step 3.

11. A process for making 6,7-dihydroxy-2,3-dihydrobenzofuran which comprises hydrogenating 6,7-dihydroxycoumaran-3-one with elemental hydrogen over a palladium catalyst in a mixture of acetic acid and ethyl acetate.

12. The process of claim 11, in which the hydrogenation is effected at a pressure of about 1 to about 10 atmospheres and a temperature of about 65° to about 150° C.

13. The process of claim 12, in which the catalyst is 10 percent palladium on charcoal and the solvent is a mixture of acetic acid and ethyl acetate containing about 5 to about 30 percent acetic acid.

14. The process of claim 11, in which the starting 6,7-dihydroxycoumaranon is a crude material obtained by refluxing ω-chloro-2,3,4-trihydroxyacetophenone with sodium acetate in ethanol, distilling off the ethanol and crystallizing the product from water without substantial further purification.

15. The process of claim 11, in which the solvent solution is distilled and the residuum of acetic acid removed by azeotropic distillation with benzene.

* * * * *